United States Patent [19]

Schwartz, deceased

[11] Patent Number: Plant 5,690

[45] Date of Patent: Mar. 18, 1986

[54] MINIATURE ROSE PLANT-SCHOBITET VARIETY

[75] Inventor: Earnest Schwartz, deceased, late of Kingsville, Md., by Hazel E. Schwartz, executrix

[73] Assignee: The Conard-Pyle Company, West Grove, Pa.

[21] Appl. No.: 634,367

[22] Filed: Jul. 25, 1984

[51] Int. Cl.[4] ..... A01H 5/00

[52] U.S. Cl. ..... Plt./8

[58] Field of Search ..... Plt./8

*Primary Examiner*—Robert E. Bagwill

*Attorney, Agent, or Firm*—Burns, Doane, Swecker & Mathis

[57] ABSTRACT

A new and distinct variety of rose plant of the Miniature class is provided which forms in abudnance attractive fully double flowers which are clear yellow in coloration. The plant is low growing, compact, well formed, and possesses semi-glossy foliage. It performs well as an outdoor garden rose, or it readily may be forced into bloom while growing in a greenhouse.

1 Drawing Figure

SUMMARY OF THE INVENTION

The new variety of Miniature rose plant of the present invention was the result of plant breeding program wherein the resulting progeny were screened for the desired characteristics.

As the result of this breeding program, a new and distinct rose variety was produced which is distinguished from its parents as well as from all other varieties known to the originator.

The new variety of Miniature rose plant of the present invention possesses the following combination of characteristics:

(a) a vigorous growth habit which forms a well-balanced, well-branched plant which commonly attains a height of less than 60 cm. and has semi-glossy foliage which exhibits greater than usual disease resistance, (b) produces fully double, well-formed flowers of clear yellow coloration, fading eventually to pale lemon yellow coloration, which are of good substance and which are produced in abundance, and (c) has an ability to be used either as a fully hardy outdoor garden rose, or to be forced into bloom in a greenhouse as a flowering pot plant.

In view of these characteristics, the new variety meets the needs of the horticultural industry for all purposes, and is particularly versatile, being well-suited to either outdoor garden or indoor greenhouse culture.

Asexual reproduction by cuttings and budding has been accomplished at West Grove, Pa. Succeeding propagations have shown that the unique combination of characteristics is fully established and is transmitted to successive generations.

The new variety has been named the SCHOBITET variety. This new variety presently is being marketed by the Conard-Pyle Company of West Grove, Pa. under the ROYAL SUNBLAZE and MINIFLORA trademarks.

BRIEF DESCRIPTION OF THE PHOTOGRAPH

The accompanying photograph shows typical specimens of the new variety of Miniature rose plant of the present invention during early July as depicted in color as true as is reasonably possible to make the same in color photograph of this nature. The specimens illustrated were budded on *Rosa multiflora* understock and were grown outdoors in a cultivated field at West Grove, Pa.

DETAILED DESCRIPTION

The plants described were grown outdoors in an open field at West Grove, Pa. while present on *Rosa multiflora* understock.

The chart used in the identification of the colors is that of The Royal Horticultural Society (R.H.S. Colour Chart).

Class: Miniature.

Plant:

*Habit.*—Low growing compact plant.

*Height.*—Commonly less than 60 cm.

Branches:

*Color.*—Young stems: Yellow-Green Group 144C with a red tinge on sun exposed side of Red Group 54A. Mature wood: Yellow-Green Group 144A.

*Thorns.*—Color on young stems: Red Group 54A at thorn base lightening to Yellow-Green Group 144C at thorn tip. Color on mature wood: Red Group 53D.

Foliage:

*Leaves.*—Usually composed of 3 to 5 leaflets per leaf, approximately 4 to 7 cm. in length with an average length of 6 cm.

*Leaflets.*—Shape: Each leaflet is elliptic to ovate in shape with an acute tip and an obtuse base, edges are serrulate. Size: Approximately 1 to 3 cm. in length with an average length of approximately 2 cm., and approximately 0.75 to 1.75 cm. in width with an average width of 1.5 cm. Color young foliage: Upper surface: Green Group 137A to 137B with red edges of Red Group 53B. Under surface: Green Group 138B with red edges of Red Group 53B. Color adult foliage: Upper surface: Green Group 137A to 137B. Under surface: Green Group 138B.

Flowers:

*Number of flowers.*—Clusters of flowers are commonly composed of 2 to 8 flowers, occasionally one flower per stem is present.

*Peduncle.*—Yellow-Green Group 144A in coloration, older peduncles may have a red tinge of Red Group 54A.

*Bud.*—Shape: Ovoid, base is rounded and top tapers to a point. Color on opening: Yellow Group 10A on both sides of the petal.

*Flower.*—Diameter: Approximately 4 to 5 cm. with an average of 4.5 cm. Color when opening: Inside of petals: Yellow Group 13A at petal base and Yellow Group 13B at petal edge. Outside of petals: Yellow Group 13B. Color when fully open: Inside of petals: Yellow Group 10A. Outside of petals: Yellow Group 10A.

*Fragrance.*—None.

*Lasting Quality.*—Average.

Development:

*Vegetation.*—Vigorous.

*Blossoming.*—Profuse.

*Resistance to disease.*—Good.

I claim:

1. A new and distinct variety of Miniature rose plant, substantially as illustrated and described, having the following combination of characteristics:

(a) a vigorous growth habit which forms a well-balanced, well-branched plant which commonly attains a height of less than 60 cm. and has semi-glossy foliage which exhibits a greater than usual disease resistance, (b) produces fully double, well-formed flowers of clear yellow coloration, fading eventually to pale lemon yellow coloration, which are of good substance and which are produced in abundance, and (c) has an ability to be used either as a fully hardy outdoor garden rose, or to be forced into bloom in a greenhouse as a flowering pot plant.

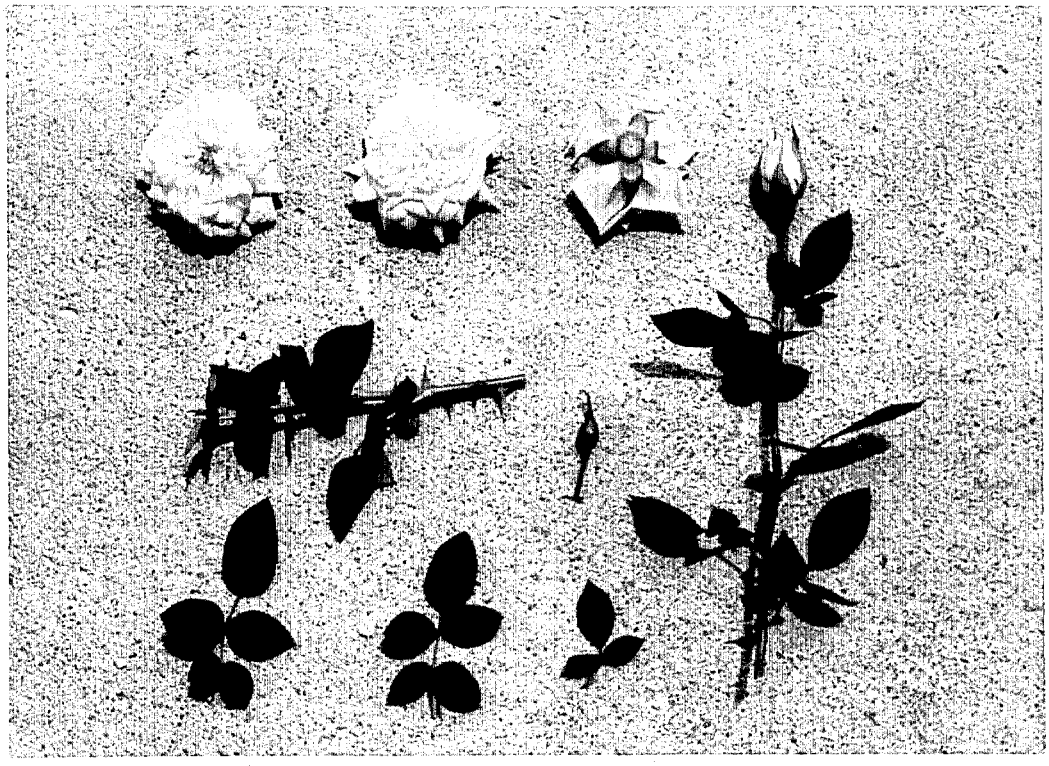

* * * * *